United States Patent
Suzuki et al.

(10) Patent No.: US 8,772,315 B2
(45) Date of Patent: Jul. 8, 2014

(54) PHARMACEUTICAL COMPOSITION FOR TREATING OVERACTIVE BLADDER

(71) Applicant: Astellas Pharma Inc., Tokyo (JP)

(72) Inventors: Masanori Suzuki, Chuo-ku (JP); Masashi Ukai, Chuo-ku (JP); Akiyoshi Ohtake, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/748,956

(22) Filed: Jan. 24, 2013

(65) Prior Publication Data
US 2013/0150402 A1 Jun. 13, 2013

Related U.S. Application Data

(63) Continuation of application No. 12/740,699, filed as application No. PCT/JP2008/069736 on Oct. 30, 2008, now abandoned.

(30) Foreign Application Priority Data

Nov. 2, 2007 (JP) ................ P2007-285802

(51) Int. Cl.
*A61K 31/426* (2006.01)

(52) U.S. Cl.
USPC ............................................. 514/305

(58) Field of Classification Search
CPC ............................................. A61K 2300/00
USPC ............................................. 514/307, 370
See application file for complete search history.

(56) References Cited

U.S. PATENT DOCUMENTS

| | | | |
|---|---|---|---|
| 6,017,927 | A | 1/2000 | Takeuchi et al. |
| 2005/0004190 | A1 | 1/2005 | Kawazoe et al. |
| 2005/0101607 | A1 | 5/2005 | Michel et al. |
| 2005/0261328 | A1 | 11/2005 | Wienrich et al. |
| 2005/0261369 | A1 | 11/2005 | Mehlburger et al. |
| 2005/0282799 | A1 | 12/2005 | Landau et al. |
| 2006/0035923 | A1 | 2/2006 | Van Meeteren et al. |
| 2006/0115540 | A1 | 6/2006 | Takasu et al. |
| 2009/0131469 | A1 | 5/2009 | Ikeda et al. |

FOREIGN PATENT DOCUMENTS

| | | |
|---|---|---|
| CA | 2 503 570 | 5/2004 |
| CA | 2 560 080 | 9/2005 |
| JP | 2006-509752 | 3/2006 |
| WO | 96/20194 | 7/1996 |
| WO | 2004/041276 | 5/2004 |
| WO | 2004/047838 | 6/2004 |
| WO | 2008/107446 | 9/2008 |

OTHER PUBLICATIONS

Berembaum, et al., "Synergy, additivism and antagonism in immunosuppression", Clin. Ex. Immunol., vol. 28 (1977) 1-18.
Tubaro et al., "Comparison of Peripherally Acting Substance for Treatment of Detrusor Overactivity: What is New; What is in the Pipeline?" EAU Update Series 2 (2004) 161-69.
Chapple, "Solifenacin provides effective antimuscarinic therapy for the complete management of overactive bladder", Exp. Opin. Pharmacother., vol. 7, No. 17 (2006) 2421-34.
Colli, et al., "Overactive bladder treatments in early phase clinical trials", Expert Opin. Investig. Drugs, vol. 16, No. 7 (2007) 999-1007.
Ohtake, et al., "Pharmacological Characterization of a New Antimuscarinic Agent, Solifenancin Succinate, in Comparison with Other Antimuscarinic Agents", Biol. Pharm. Bull., vol. 30, No. 1 (2007) 54-8.
Okutsu, et al., "Effects of Intravenously and Orally Administered Solifenacin Succinate (YM905) on Carbachol-Induced Intravesical Pressure Elevations and Salivary Secretion in Mice", Biol. Pharm. Bull., vol. 30, No. 12 (2007) 2324-27.
Takasu, et al., "Effect of (R)-2-(2-Aminothiazol-4-yl)-4'-{2-[(2-hydroxy-2-phenylethyl)amino]ethyl} Acetanilide (YM178), a Novel Selective β3-Adrenoceptor Agonist, on Bladder Function", J. Pharmacol. Exp. Therap., vol. 321, No. 2 (2007) 642-47.
Tiwari, et al., "Current and emerging investigational medical therapies for the treatment of overactive bladder", Expert Opin. Investig. Drugs, vol. 15, No. 9 (2006) 1017-37.
Tubaro, et al., "Comparison of Peripherally Acting Substance for Treatment of Detrusor Overacitvity: What is New; What is in the Pipeline", EUA Update Series 2 (2004) 161-69.

*Primary Examiner* — Shirley V Gembeh
(74) *Attorney, Agent, or Firm* — Fitzpatrick, Cella, Harper & Scinto

(57) ABSTRACT

A pharmaceutical composition comprising (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof, as active ingredients, in particular for improving various symptoms accompanying overactive bladder, such as urinary urgency, pollakiuria and/or urinary incontinence.

16 Claims, 1 Drawing Sheet

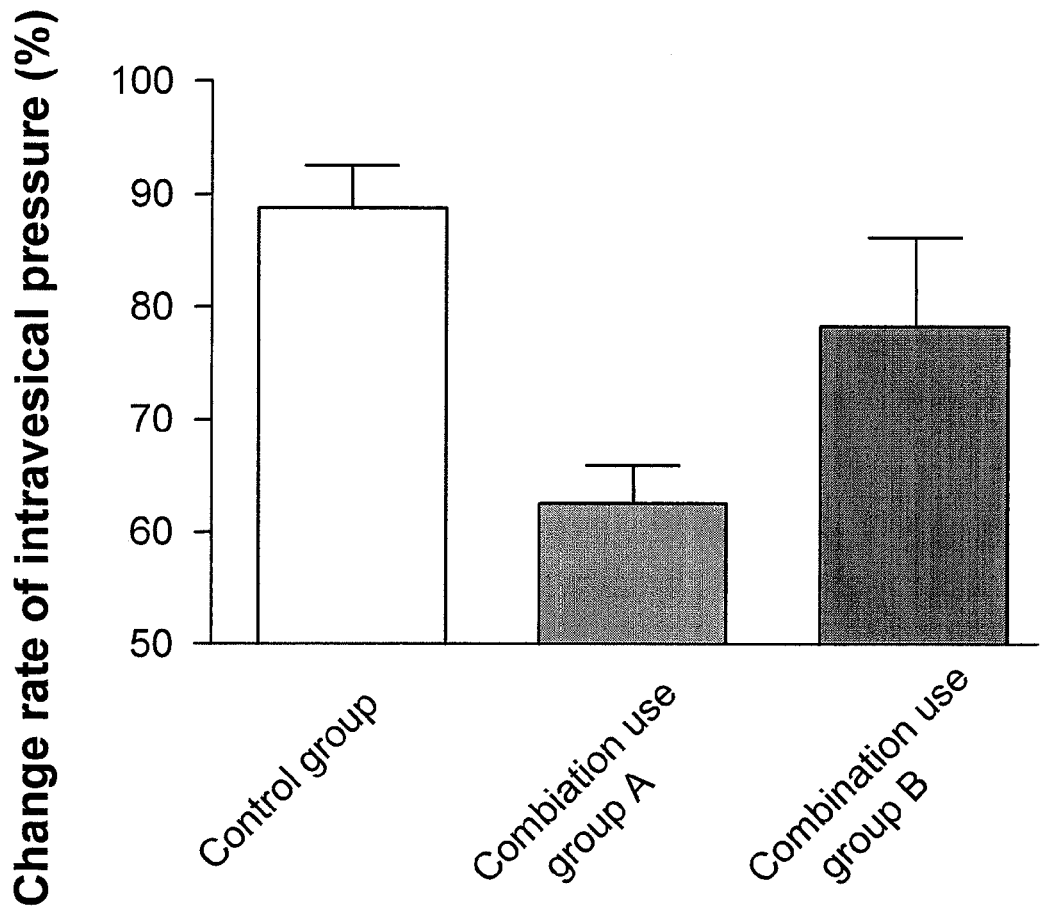

PHARMACEUTICAL COMPOSITION FOR TREATING OVERACTIVE BLADDER

This application is a continuation of application Ser. No. 12/740,699 filed Apr. 30, 2010, which in turn is the national phase of PCT Application No. PCT/JP2008/069736 filed Oct. 30, 2008, which claims priority of Japanese Application No. P2007-285802 filed Nov. 2, 2007.

TECHNICAL FIELD

The present invention relates to a pharmaceutical, in particular, a pharmaceutical composition which is useful as a therapeutic agent for symptoms accompanying overactive bladder such as urinary urgency, pollakiuria and/or urinary incontinence, particularly a pharmaceutical composition containing (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof, as active ingredients. In addition, the present invention relates to combination use and combination therapy of (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof for treating symptoms accompanying overactive bladder such as urinary urgency, pollakiuria and/or urinary incontinence.

BACKGROUND ART

Overactive bladder is defined as a disease name which causes urinary urgency frequently. Although prostatic hyperplasia may be exemplified as one of the causes for overactive bladder, there are many cases where the cause is ambiguous, which are called idiopathic overactive bladder. Further, although overactive bladder is sometimes accompanied by pollakiuria and urinary incontinence, it is not always limited to the disease accompanied by pollakiuria and urinary incontinence. That is, in the case of mild overactive bladder, a patient is sensitive to the sense of wishing to urinate and frequently has a sense of wishing to urinate but, actually, can hold their urine for a certain period of time. However, even in the case of mild overactive bladder, there is a strong demand for improvement in view of patient QOL (Quality of Life).

On the other hand, severe overactive bladder is sometimes accompanied by pollakiuria and urinary incontinence. Pollakiuria is a state where number of times of urination is more than normal and is usually twice or more at night and eight times or more during 24 hours. Urinary incontinence is defined as a state where there is a problem socially or hygienically due to an involuntary leakage of urine, and is classified into abdominal pressure urinary incontinence that takes place when abdominal pressure is applied such as during coughing or sneezing, urge urinary incontinence in which need of urinate takes place suddenly, with urine leakage before a patient reaches a toilet, mixed-type urinary incontinence of abdominal pressure urinary incontinence with urge urinary incontinence, and the like.

Anticholinergic agents are mainly used for treating symptoms accompanying overactive bladder, but there are some cases where expression of side effects accompanying the anticholinergic actions, such as dry mouth, constipation, blurred vision, or the like, is exhibited. Therefore, it cannot be stated that satisfactory therapeutic results are always achieved. Further, a $\beta_3$ adrenergic receptor agonist is under a clinical test as a therapeutic agent for overactive bladder at present, but in view of expression of its effects or side effects as a pharmaceutical product, there are still many unclear factors.

Under these circumstances, there is a document which discloses treatment of bladder dysfunction by a pharmaceutical composition containing an antimuscarinic agent and a $\beta_3$ adrenergic receptor agonist (Patent Document 1).

This document cites a large number of compounds, regarding each of an antimuscarinic agent and a $\beta_3$ adrenergic receptor agonist to be combined, but has no specific description of combination of (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof according to the present invention.

There is a disclosure that (R)-2-(2-aminothiazol-4-yl)-4'-{2-[(2-hydroxy-2-phenylethyl)amino]ethyl}acetanilide has a $\beta_3$ adrenergic receptor agonistic action and is useful as a therapeutic agent for overactive bladder when used as a single agent (Patent Document 2). In addition, the chemical structure of this compound is as follows and is known as YM178.

[Chem. 1]

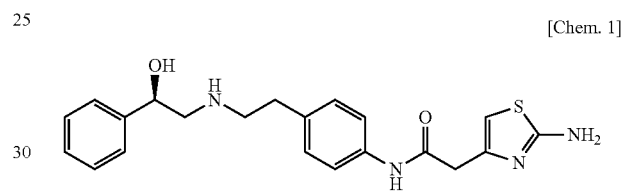

There is a disclosure that (3R)-quinuclidin-3-yl (1S)-1-phenyl-1,2,3,4-tetrahydroisoquinoline-2-carboxylate has muscarinic $M_3$ receptor antagonistic activities and is useful as a therapeutic agent for unstable bladder when used as a single agent (Patent Document 3). Further, the "unstable bladder" as used in Patent Document 3 has the same meaning as "overactive bladder". In addition, the chemical structure of this compound is as follows and is also known as solifenacin or YM905.

[Chem. 2]

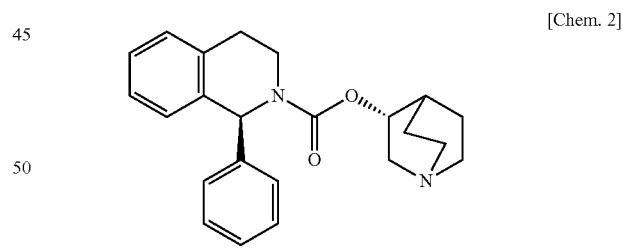

[Patent Document 1] Pamphlet of International Publication WO 2004/047838
[Patent Document 2] Pamphlet of International Publication WO 2004/041276
[Patent Document 3] Pamphlet of International Publication WO 96/20194

DISCLOSURE OF INVENTION

Problem that the Invention is to Solve

A pharmaceutical composition, specifically a therapeutic agent for overactive bladder, containing (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof, is provided.

Furthermore, combination use and combination therapy of (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof, for treating overactive bladder, are provided.

Means for Solving the Problem

The present inventors have investigated a therapeutic agent for overactive bladder containing an anticholinergic agent and a $\beta_3$ adrenergic receptor agonist, and as a result, they have found that expression of an excellent therapeutic effect for overactive bladder is achieved particularly by combination of (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof, thereby completing the present invention.

That is, the present invention relates to:

[1]
a pharmaceutical composition comprising (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof, as active ingredients;

[2]
the pharmaceutical composition of [1], wherein the (R)-2-(2-aminothiazol-4-yl)-4'-{2-[(2-hydroxy-2-phenylethyl)amino]ethyl}acetanilide or a pharmaceutically acceptable salt thereof is (R)-2-(2-aminothiazol-4-yl)-4'-{2-[(2-hydroxy-2-phenylethyl)amino]ethyl}acetanilide;

[3]
the pharmaceutical composition of either of [1] or [2], wherein the (3R)-quinuclidin-3-yl (1S)-1-phenyl-1,2,3,4-tetrahydroisoquinoline-2-carboxylate or a pharmaceutically acceptable salt thereof is (3R)-quinuclidin-3-yl (1S)-1-phenyl-1,2,3,4-tetrahydroisoquinoline-2-carboxylate succinate;

[4]
the pharmaceutical composition of any one of [1] to [3], further comprising a pharmaceutically acceptable excipient;

[5]
a pharmaceutical composition comprising (R)-2-(2-aminothiazol-4-yl)-4'-{2-[(2-hydroxy-2-phenylethyl)amino]ethyl}acetanilide or a pharmaceutically acceptable salt thereof at an amount of 10 mg to 100 mg in terms of (R)-2-(2-aminothiazol-4-yl)-4'-{2-[(2-hydroxy-2-phenylethyl)amino]ethyl}acetanilide, and (3R)-quinuclidin-3-yl (1S)-1-phenyl-1,2,3,4-tetrahydroisoquinoline-2-carboxylate or a pharmaceutically acceptable salt thereof at an amount of 0.5 mg to 10 mg in terms of (3R)-quinuclidin-3-yl (1S)-1-phenyl-1,2,3,4-tetrahydroisoquinoline-2-carboxylate succinate, as active ingredients;

[6]
the pharmaceutical composition of [5], comprising 10 mg to 100 mg of (R)-2-(2-aminothiazol-4-yl)-4'-{2-[(2-hydroxy-2-phenylethyl)amino]ethyl}acetanilide, and 0.5 mg to 10 mg of (3R)-quinuclidin-3-yl (1S)-1-phenyl-1,2,3,4-tetrahydroisoquinoline-2-carboxylate succinate;

[7]
the pharmaceutical composition of any one of [1] to [6], which is a therapeutic agent for urinary urgency, pollakiuria and/or urinary incontinence accompanying overactive bladder;

[8]
the pharmaceutical composition of any one of [1] to [7], which is a preparation for oral administration;

[9]
a method for treating urinary urgency, pollakiuria and/or urinary incontinence accompanying overactive bladder, comprising administering effective amounts of each of (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof;

[10]
the method for treating of [9], comprising administering effective amounts of each of (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof, simultaneously or at a time interval;

[11]
use of (3R)-quinuclidin-3-yl (1S)-1-phenyl-1,2,3,4-tetrahydroisoquinoline-2-carboxylate or a pharmaceutically acceptable salt thereof, for the manufacture of a therapeutic agent for urinary urgency, pollakiuria and/or urinary incontinence accompanying overactive bladder, which is used in combination with (R)-2-(2-aminothiazol-4-yl)-4'-{2-[(2-hydroxy-2-phenylethyl)amino]ethyl}acetanilide or a pharmaceutically acceptable salt thereof;

[12]
use of (R)-2-(2-aminothiazol-4-yl)-4'-{2-[(2-hydroxy-2-phenylethyl)amino]ethyl}acetanilide or a pharmaceutically acceptable salt thereof for the manufacture of a therapeutic agent for urinary urgency, pollakiuria and/or urinary incontinence accompanying overactive bladder, which is used in combination with (3R)-quinuclidin-3-yl (1S)-1-phenyl-1,2,3,4-tetrahydroisoquinoline-2-carboxylate or a pharmaceutically acceptable salt thereof;

[13]
a pharmaceutical composition comprising (R)-2-(2-aminothiazol-4-yl)-4'-{2-[(2-hydroxy-2-phenylethyl)amino]ethyl}acetanilide or a pharmaceutically acceptable salt thereof as an active ingredient, which is used in combination with (3R)-quinuclidin-3-yl (1S)-1-phenyl-1,2,3,4-tetrahydroisoquinoline-2-carboxylate or a pharmaceutically acceptable salt thereof;

[14]
a pharmaceutical composition comprising (3R)-quinuclidin-3-yl (1S)-1-phenyl-1,2,3,4-tetrahydroisoquinoline-2-carboxylate or a pharmaceutically acceptable salt thereof as an active ingredient, which is used in combination with (R)-2-(2-aminothiazol-4-yl)-4'-{2-[(2-hydroxy-2-phenylethyl)amino]ethyl}acetanilide or a pharmaceutically acceptable salt thereof.

Further, the present invention relates to a pharmaceutical composition for treating overactive bladder containing (R)-2-(2-aminothiazol-4-yl)-4'-{2-[(2-hydroxy-2-phenylethyl)amino]ethyl}acetanilide or a pharmaceutically acceptable salt thereof, and (3R)-quinuclidin-3-yl (1S)-1-phenyl-1,2,3,4-tetrahydroisoquinoline-2-carboxylate or a pharmaceutically acceptable salt thereof, that is, a therapeutic agent for overactive bladder containing (R)-2-(2-aminothiazol-4-yl)-4'-{2-[(2-hydroxy-2-phenylethyl)amino]ethyl}acetanilide or a pharmaceutically acceptable salt thereof, and (3R)-quinuclidin-3-yl (1S)-1-phenyl-1,2,3,4-tetrahydroisoquinoline-2-carboxylate or a pharmaceutically acceptable salt thereof.

In addition, the present invention relates to use of (R)-2-(2-aminothiazol-4-yl)-4'-{2-[(2-hydroxy-2-phenylethyl)amino]ethyl}acetanilide or a pharmaceutically acceptable salt thereof, and (3R)-quinuclidin-3-yl (1S)-1-phenyl-1,2,3,4-tetrahydroisoquinoline-2-carboxylate or a pharmaceutically acceptable salt thereof, for the manufacture of a therapeutic agent for overactive bladder, and a method for treating overactive bladder, comprising administering to a patient effective amounts of (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof.

Effects of the Invention

A pharmaceutical composition containing (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof, as active ingredients, can be used as a therapeutic agent for urinary urgency, pollakiuria and/or urinary incontinence accompanying overactive bladder.

BRIEF DESCRIPTION OF THE DRAWINGS

FIG. 1 is a graph showing a change rate to the increase in the intravesical pressure caused by carbachol shown in Examples, for each of the administration groups.

BEST MODE FOR CARRYING OUT THE INVENTION

Hereinbelow, the present invention will be described in detail.

In the present specification, the "therapeutic agent for overactive bladder" refers to a drug which mitigates especially the frequent occurrence of urinary urgency of a patient, and thus makes the number of times of urination and the state of urination into a more normal state. It goes without saying that it includes not only a therapeutic agent for overactive bladder accompanying prostatic hyperplasia but also a therapeutic agent for overactive bladder accompanied with urinary urgency, urinary incontinence, and pollakiuria.

(R)-2-(2-Aminothiazol-4-yl)-4'-{2-[(2-hydroxy-2-phenylethyl)amino]ethyl}acetanilide or a pharmaceutically acceptable salt thereof which is an active ingredient of the pharmaceutical composition of the present invention is easily available, for example, by a method described in Pamphlet of International Publication WO 99/20607, a method apparent to a person skilled in the art, or a modified method thereof.

Also, (3R)-quinuclidin-3-yl (1S)-1-phenyl-1,2,3,4-tetrahydroisoquinoline-2-carboxylate or a pharmaceutically acceptable salt thereof which is an active ingredient of the pharmaceutical composition of the present invention is easily available, for example, by a method described in Patent Document 3 as described above, a method apparent to a person skilled in the art, or a modified method thereof.

The "pharmaceutically acceptable salt" in "(R)-2-(2-aminothiazol-4-yl)-4'-{2-[(2-hydroxy-2-phenylethyl)amino]ethyl}acetanilide or a pharmaceutically acceptable salt thereof" and "(3R)-quinuclidin-3-yl (1S)-1-phenyl-1,2,3,4-tetrahydroisoquinoline-2-carboxylate or a pharmaceutically acceptable salt thereof" each refers to salts with acids described in Pamphlet of International Publication WO 99/20607, or Patent Document 3 as described above, and specific examples thereof include acid addition salts with an inorganic acid such as hydrochloric acid, hydrobromic acid, hydroiodic acid, sulfuric acid, nitric acid, phosphoric acid, and the like or an organic acid such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditolyl tartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like, and organic bases such as methylamine, ethylamine, ethanolamine, lysine, ornithine, and the like, salts with various amino acids and amino acid derivatives such as acetylleucine and the like, ammonium salts, and others.

The "(R)-2-(2-aminothiazol-4-yl)-4'-{2-[(2-hydroxy-2-phenylethyl)amino]ethyl}acetanilide or a pharmaceutically acceptable salt thereof" and "(3R)-quinuclidin-3-yl (1S)-1-phenyl-1,2,3,4-tetrahydroisoquinoline-2-carboxylate or a pharmaceutically acceptable salt thereof" may be one of various hydrates and solvates, and polymorphism, and they are each included in the active ingredients of the pharmaceutical composition of the present invention. In addition, the present invention includes a pharmaceutical composition containing compounds that are labeled with various radioactive or non-radioactive isotopes.

Certain embodiments of the present invention are shown below.

(1) Among the pharmaceutical composition or the pharmaceutical composition for treating overactive bladder, the method for treating urinary urgency, pollakiuria and/or urinary incontinence accompanying overactive bladder, or the use for the manufacture of a therapeutic agent for urinary urgency, pollakiuria and/or urinary incontinence accompanying overactive bladder which is used in combination with (3R)-quinuclidin-3-yl (1S)-1-phenyl-1,2,3,4-tetrahydroisoquinoline-2-carboxylate or a pharmaceutically acceptable salt thereof, of the present invention; the pharmaceutical composition or the pharmaceutical composition for treating overactive bladder, the method for treating urinary urgency, pollakiuria and/or urinary incontinence accompanying overactive bladder, or the use for the manufacture of a therapeutic agent for urinary urgency, pollakiuria and/or urinary incontinence accompanying overactive bladder which is used in combination with (3R)-quinuclidin-3-yl (1S)-1-phenyl-1,2,3,4-tetrahydroisoquinoline-2-carboxylate or a pharmaceutically acceptable salt thereof, wherein the (R)-2-(2-aminothiazol-4-yl)-4'-{2-[(2-hydroxy-2-phenylethyl)amino]ethyl}acetanilide or a pharmaceutically acceptable salt thereof is (R)-2-(2-aminothiazol-4-yl)-4'-{2-[(2-hydroxy-2-phenylethyl)amino]ethyl}acetanilide.

(2) Among the pharmaceutical composition or the pharmaceutical composition for treating overactive bladder, the method for treating urinary urgency, pollakiuria and/or urinary incontinence accompanying overactive bladder, or the use for the manufacture of a therapeutic agent for urinary urgency, pollakiuria and/or urinary incontinence accompanying overactive bladder which is used in combination with (R)-2-(2-aminothiazol-4-yl)-4'-{2-[(2-hydroxy-2-phenylethyl)amino]ethyl}acetanilide or a pharmaceutically acceptable salt thereof, of the present invention; the pharmaceutical composition or the pharmaceutical composition for treating overactive bladder, the method for treating urinary urgency, pollakiuria and/or urinary incontinence accompanying overactive bladder, or the use for the manufacture of a therapeutic agent for urinary urgency, pollakiuria and/or urinary incontinence accompanying overactive bladder which is used in combination with (R)-2-(2-aminothiazol-4-yl)-4'-{2-[(2-hydroxy-2-phenylethyl)amino]ethyl}acetanilide or a pharmaceutically acceptable salt thereof, wherein the (3R)-quinuclidin-3-yl (1S)-1-phenyl-1,2,3,4-tetrahydroisoquinoline-2-carboxylate or a pharmaceutically acceptable salt thereof is (3R)-quinuclidin-3-yl (1S)-1-phenyl-1,2,3,4-tetrahydroisoquinoline-2-carboxylate succinate.

(3) Among the pharmaceutical composition or the pharmaceutical composition for treating overactive bladder, the method for treating urinary urgency, pollakiuria and/or urinary incontinence accompanying overactive bladder, or the use for the manufacture of a therapeutic agent for urinary urgency, pollakiuria and/or urinary incontinence accompanying overactive bladder which is used in combination with (3R)-quinuclidin-3-yl (1S)-1-phenyl-1,2,3,4-tetrahydroisoquinoline-2-carboxylate or a pharmaceutically acceptable salt thereof, of the present invention; the pharmaceutical composition or the pharmaceutical composition for treating overactive bladder, the method for treating urinary urgency, pollakiuria and/or urinary incontinence accompanying overactive bladder, or the use for the manufacture of a therapeutic agent for urinary urgency, pollakiuria and/or urinary incontinence accompanying overactive bladder which is used in combination with (3R)-quinuclidin-3-yl (1S)-1-phenyl-1,2,3,4-tetrahydroisoquinoline-2-carboxylate or a pharmaceutically acceptable salt thereof, wherein the amount of (R)-2-(2-aminothiazol-4-yl)-4'-{2-[(2-hydroxy-2-phenylethyl)amino]ethyl}acetanilide or a pharmaceutically acceptable salt thereof to be contained is from 10 mg to 100 mg in terms of (R)-2-(2-aminothiazol-4-yl)-4'-{2-[(2-hydroxy-2-phenylethyl)amino]ethyl}acetanilide. In another embodiment, the pharmaceutical composition or the pharmaceutical composition for treating overactive bladder, the method for treating urinary urgency, pollakiuria and/or urinary incontinence accompanying overactive bladder, or the use for the manufacture of a therapeutic agent for urinary urgency, pollakiuria and/or urinary incontinence accompanying overactive bladder which is used in combination with (3R)-quinuclidin-3-yl (1S)-1-phenyl-1,2,3,4-tetrahydroisoquinoline-2-carboxylate or a pharmaceutically acceptable salt thereof, wherein the amount of (R)-2-(2-aminothiazol-4-yl)-4'-{2-[(2-hydroxy-2-phenylethyl)amino]ethyl}acetanilide or a pharmaceutically acceptable salt thereof to be contained is 10 mg, 25 mg, 50 mg, or 100 mg in terms of (R)-2-(2-aminothiazol-4-yl)-4'-{2-[(2-hydroxy-2-phenylethyl)amino]ethyl}acetanilide.

(4) Among the pharmaceutical composition or the pharmaceutical composition for treating overactive bladder, the method for treating urinary urgency, pollakiuria and/or urinary incontinence accompanying overactive bladder, or the use for the manufacture of a therapeutic agent for urinary urgency, pollakiuria and/or urinary incontinence accompanying overactive bladder which is used in combination with (R)-2-(2-aminothiazol-4-yl)-4'-{2-[(2-hydroxy-2-phenylethyl)amino]ethyl}acetanilide or a pharmaceutically acceptable salt thereof of, the present invention; the pharmaceutical composition or the pharmaceutical composition for treating overactive bladder, the method for treating urinary urgency, pollakiuria and/or urinary incontinence accompanying overactive bladder, or the use for the manufacture of a therapeutic agent for urinary urgency, pollakiuria and/or urinary incontinence accompanying overactive bladder which is used in combination with (R)-2-(2-aminothiazol-4-yl)-4'-{2-[(2-hydroxy-2-phenylethyl)amino]ethyl}acetanilide or a pharmaceutically acceptable salt thereof, wherein the amount of (3R)-quinuclidin-3-yl (1S)-1-phenyl-1,2,3,4-tetrahydroisoquinoline-2-carboxylate or a pharmaceutically acceptable salt thereof to be contained is from 0.5 mg to 10 mg in terms of (3R)-quinuclidin-3-yl (1S)-1-phenyl-1,2,3,4-tetrahydroisoquinoline-2-carboxylate succinate. In another embodiment, the pharmaceutical composition or the pharmaceutical composition for treating overactive bladder, the method for treating urinary urgency, pollakiuria and/or urinary incontinence accompanying overactive bladder, or the use for the manufacture of a therapeutic agent for urinary urgency, pollakiuria and/or urinary incontinence accompanying overactive bladder which is used in combination with (R)-2-(2-aminothiazol-4-yl)-4'-{2-[(2-hydroxy-2-phenylethyl)amino]ethyl}acetanilide or a pharmaceutically acceptable salt thereof, wherein the amount of (3R)-quinuclidin-3-yl (1S)-1-phenyl-1,2,3,4-tetrahydroisoquinoline-2-carboxylate or a pharmaceutically acceptable salt thereof to be contained is 0.5 mg, 1 mg, 2.5 mg, 3 mg, 5 mg, 6 mg, 9 mg, or 10 mg in terms of (3R)-quinuclidin-3-yl (1S)-1-phenyl-1,2,3,4-tetrahydroisoquinoline-2-carboxylate succinate.

(5) The pharmaceutical composition or the pharmaceutical composition for treating overactive bladder for oral administration, the method for treating urinary urgency, pollakiuria and/or urinary incontinence accompanying overactive bladder by oral administration, the use for the manufacture of a therapeutic agent for oral administration for urinary urgency, pollakiuria and/or urinary incontinence accompanying overactive bladder which is used in combination with (R)-2-(2-aminothiazol-4-yl)-4'-{2-[(2-hydroxy-2-phenylethyl)amino]ethyl}acetanilide or a pharmaceutically acceptable salt thereof, or the use for the manufacture of a therapeutic agent for oral administration for urinary urgency, pollakiuria and/or urinary incontinence accompanying overactive bladder which is used in combination with (3R)-quinuclidin-3-yl (1S)-1-phenyl-1,2,3,4-tetrahydroisoquinoline-2-carboxylate or a pharmaceutically acceptable salt thereof.

(6) The pharmaceutical composition or the pharmaceutical composition for treating overactive bladder, the method for treating urinary urgency, pollakiuria and/or urinary incontinence accompanying overactive bladder by oral administration, the use for the manufacture of a therapeutic agent for oral administration for urinary urgency, pollakiuria and/or urinary incontinence accompanying overactive bladder which is used in combination with (R)-2-(2-aminothiazol-4-yl)-4'-{2-[(2-hydroxy-2-phenylethyl)amino]ethyl}acetanilide or a pharmaceutically acceptable salt thereof, or the use for the manufacture of a therapeutic agent for oral administration for urinary urgency, pollakiuria and/or urinary incontinence accompanying overactive bladder which is used in combination with (3R)-quinuclidin-3-yl (1S)-1-phenyl-1,2,3,4-tetrahydroisoquinoline-2-carboxylate or a pharmaceutically acceptable salt thereof; which is a combination of two or more of (1) to (5) above.

The pharmaceutical composition of the present invention can be prepared using (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof, and pharmaceutical carriers, excipients, or other additives, that are usually used for preparation, by a generally used method. The administration can be any form of oral administration via tablets, pills, capsules, granules, powders, liquid preparations, or the like, or parenteral administration via injections such as intraarticular, intravenous, intramuscular or the like, suppositories, eye drops, eye ointments, percutaneous liquid preparations, ointments, percutaneous patches, transmucosal liquid preparations, transmucosal patches, inhalations, and the like, and in a certain embodiment, oral administration can be mentioned.

As the solid composition for oral administration, tablets, powders, granules, or the like are used. In such a solid composition, the active ingredients are mixed with at least one inert excipient. According to a conventional method, the composition may contain inert additives, for example, a lubricant, a disintegrator, a stabilizing agent, and a solubilizing aid. As occasion demands, the tablets or the pills may be coated with a sugar coating, or a film of gastric or enteric material.

The liquid composition for oral administration includes pharmaceutically acceptable emulsions, solutions, suspensions, syrups, elixirs, or the like, and contains a generally used inert diluent such as purified water or ethanol. In addition to the inert diluent, this liquid composition may contain an auxiliary agent such as a solubilizing agent, a moistening agent, and a suspending agent, a sweetener, a flavor, an aroma, and an antiseptic.

The injections for parenteral administration include sterile aqueous or non-aqueous liquid preparations, suspensions and emulsions. The aqueous solvent includes, for example, distilled water for injection and physiological saline. Examples of the non-aqueous solvent include propylene glycol, polyethylene glycol, plant oils such as olive oil, alcohols such as ethanol, Polysorbate 80 (Japanese Pharmacopeia), and the like. Such a composition may further contain a tonicity agent, an antiseptic, a moistening agent, an emulsifying agent, a dispersing agent, a stabilizing agent, or a solubilizing agent. These are sterilized, for example, by filtration through a bacteria retaining filter, blending of a bactericide, or irradiation. Additionally, these can also be used by preparing a sterile solid composition, and dissolving or suspending it in sterile water or a sterile solvent for injection prior to its use.

The agent for external use includes ointments, plasters, creams, jellies, cataplasms, sprays, lotions, eye drops, eye ointments, and the like. The agents contain generally used ointment bases, lotion bases, aqueous or non-aqueous liquid preparations, suspensions, emulsions, and the like. Examples of the ointment bases or the lotion bases include polyethylene glycol, propylene glycol, white vaseline, bleached bee wax, polyoxyethylene hydrogenated castor oil, glyceryl monostearate, stearyl alcohol, cetyl alcohol, lauromacrogol, sorbitan sesquioleate, and the like.

As the transmucosal agents such as an inhalation, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate propellant, for example, a suitable gas such as chlorofluoroalkane, hydrofluoroalkane, carbon dioxide, and the like, or other forms.

The combination use in the present invention may be administered simultaneously, separately and successively, or at a desired time interval. In the case of simultaneous administration, the preparation may be a blend, that is, a preparation containing both active ingredients in a single preparation, or alternatively, the separate preparations for each of the active ingredients may be prepared individually and then administered simultaneously.

EXAMPLES

The pharmacological activity for the combination use of the active ingredients of the pharmaceutical composition according to the present invention was confirmed by the following test.

Example 1

<Method>

A rat was fixed to a dorsal position under pentobarbital anesthesia (60 mg/kg ip), and a catheter (PE-50) for carbachol administration was inserted into the femoral vein. Further, the upper abdomen was subjected to median laparotomy, a catheter for drug administration (PE-50) was inserted into the duodenum, and a catheter (PE-50) was inserted into the bladder from external urethral orifice, and then ligated with distal urethra. The intravesical pressure was measured by an amplifier for pressure measurement (AP-601 G) through a pressure transducer (TP-400T) from the catheter inserted into the bladder. After surgery, physiological saline was injected into the bladder through the catheter for measurement of an intravesical pressure until the intravesical pressure becomes about 10 cm $H_2O$. At this time, the total amount of the physiological saline injected was set to 1 mL or less. Carbachol (10 μg/kg iv) was administered twice at a 20 minutes interval, confirming that the reaction became stable. After 10 minutes from the second carbachol administration, a drug was administered into the duodenum.

The drugs for the three groups examined are as follows.
(1) "Control Group":
5% Dimethylacetamide and 5% aqueous solution containing Cremophor 5 mL/kg id
(2) "Combination Use Group A":
Combination use of (3R)-quinuclidin-3-yl (1S)-1-phenyl-1,2,3,4-tetrahydroisoquinoline-2-carboxylate succinate 0.2 mg/kg id and (R)-2-(2-aminothiazol-4-yl)-4'-{2-[(2-hydroxy-2-phenylethyl)amino]ethyl}acetanilide 2 mg/kg id
(3) "Combination Use Group B":
Combination use of propiverine hydrochloride 0.3 mg/kg id and (−)-ethyl-2-[4-(2-{[(1S,2R)-2-hydroxy-2-(4-hydroxyphenyl)-1-methylethyl]amino}ethyl)-2,5-dimethylphenyloxy]acetate monohydrochloride 0.87 mg/kg id After 30 minutes from drug administration, carbachol (10 μg/kg iv) was administered. The intravesical pressure which had increased by carbachol administration (second administration) 10 minutes before drug administration was taken as a pre-administration value, whereas the intravesical pressure which had increased by carbachol administration after 30 minutes from drug administration was taken as a post-administration value. Effects of the drug were evaluated with change rates (%), to the pre-administration value, of the intravesical pressure which had increased by carbachol administration.

The dose of each drug was set based on the following grounds.
(a) (3R)-Quinuclidin-3-yl (1S)-1-phenyl-1,2,3,4-tetrahydroisoquinoline-2-carboxylate succinate:

A value obtained by dividing 10 mg of a maximum dose clinically used at present by 50. Accordingly, 0.2 mg/kg of the dose used in the above-described test corresponds to a dose per unit weight when an adult weight is assumed to be 50 kg.

(b) (R)-2-(2-Aminothiazol-4-yl)-4'-{2-[(2-hydroxy-2-phenylethyl)amino]ethyl}acetanilide:

A value obtained by dividing 100 mg of a dose as expected to be a maximum dose among the doses clinically used at present by 50. Accordingly, 2 mg/kg of the dose used in the above-described test corresponds to a dose per unit weight when an adult weight is assumed to be 50 kg.

(c) Propiverine Hydrochloride:

A value obtained by dividing 15.000 mg of a dose of propiverine hydrochloride in the combination of Example 4 described in Patent Document 1 by 50. Accordingly, 0.3 mg/kg of the dose used in the above-described test corresponds to a dose per unit weight when an adult weight is assumed to be 50 kg.

(d) (−)-Ethyl-2-[4-(2-{[(1S,2R)-2-hydroxy-2-(4-hydroxyphenyl)-1-methylethyl]amino}ethyl)-2,5-dimethylphenyloxy]acetate monohydrochloride: A value obtained by dividing 43.640 mg of a dose of (−)-ethyl-2-[4-(2-{[(1S,2R)-2-hydroxy-2-(4-hydroxyphenyl)-1-methylethyl]amino}ethyl)-2,5-dimethylphenyloxy]acetate monohydrochloride in the combination of Example 4 described in Patent Document 1 by 50. Accordingly, 0.87 mg/kg of the dose used in the above-described test corresponds to a dose per unit weight when an adult weight is assumed to be 50 kg.

<Results>

In the control group, the change rate of the intravesical pressure which had increased by carbachol (10 µg/kg iv) was 88.8±3.8%. On the other hand, in the combination use group A in which the active ingredients of the pharmaceutical composition according to the present invention were used in combination, the change rate of the intravesical pressure which had increased by carbachol (10 µg/kg iv) was 62.6±3.3%, which was less than a change rate of the control group. Further, in the combination use group B in which the active ingredients of Example 4 described in Patent Document 1 were used in combination, the change rate of the intravesical pressure which had increased by carbachol (10 µg/kg iv) was 78.4±7.8%, and it was clearly demonstrated that the change rate relative to the control group was small, as compared with the combination use group A in which the active ingredients of the pharmaceutical composition according to the present invention were used in combination, and the combination use group A had an inhibitory action on the increase in the intravesical pressure caused by carbachol.

The pharmaceutical composition according to the present invention can be prepared, for example, by the following formulation, and its effect can be evaluated, for example, by the method described in Examples above or an improved or modified method thereof.

Example 2

Preparation of the Film-Coated Tablet According to the Present Invention

Hydroxypropylmethyl cellulose 2910 (200 parts) is dissolved under stirring in water (180 parts) with an air motor agitator (AM-GC-1, manufactured by Chuo-Rika Machine) to prepare a binder solution. (3R)-quinuclidin-3-yl (1S)-1-phenyl-1,2,3,4-tetrahydroisoquinoline-2-carboxylate succinate (125 parts), (R)-2-(2-aminothiazol-4-yl)-4'-{2-[(2-hydroxy-2-phenylethyl)amino]ethyl}acetanilide (1250 parts), lactose (2625 parts), and corn starch (750 parts) are mixed with a mixer (Type DC, manufactured by Astellas Pharma Inc.). The mixture is put into a fluidized bed granulation machine (WSG-5 manufactured by Powlec), and the binder solution is sprayed for granulation and then dried to obtain a granulated product. Magnesium stearate (12 parts) is added to the dried granulated product (1188 parts), and mixed with a mixer. Then, this mixture is compressed with a pestle and mortar having a diameter of 8 mm, using a rotary tableting machine (HTP-22 manufactured by Hata Tekkosho) to obtain 200 mg of a tablet. This tablet (800 parts) is sprayed and coated with a solution prepared by dissolving/dispersing hydroxypropylmethyl cellulose 2910 (84.3 parts), Macrogol 6000 (15.8 parts), talc (25.3 parts), titanium oxide (10.5 parts), and red iron sesquioxide (0.03 part) in water (1223 parts), using an aerated coating machine (high coater HCT-30 manufactured by Freund Industry Corporation) until the amount of the coating agent became 2.7% of the tablet weight, to obtain a film-coated tablet.

Example 3

Preparation of the Capsule According to the Present Invention (1)

(3R)-Quinuclidin-3-yl (1S)-1-phenyl-1,2,3,4-tetrahydroisoquinoline-2-carboxylate succinate (125 parts), (R)-2-(2-aminothiazol-4-yl)-4'-{2-[(2-hydroxy-2-phenylethyl)amino]ethyl}acetanilide (1250 parts), and lactose (3625 parts) are mixed with a mixer (Type DC, manufactured by Astellas Pharma Inc.). 200 mg of this mixture is filled into a capsule (gelatin hard capsule No. 4, manufactured by Capsugel Japan Inc.) with a small-scale capsule filling machine (propyl, manufactured by Capsugel Japan Inc.) to obtain a capsule.

Example 4

Preparation of the Capsule According to the Present Invention (2)

(3R)-Quinuclidin-3-yl (1S)-1-phenyl-1,2,3,4-tetrahydroisoquinoline-2-carboxylate succinate (62.5 parts), (R)-2-(2-aminothiazol-4-yl)-4'-{2-[(2-hydroxy-2-phenylethyl)amino]ethyl}acetanilide (625 parts), and lactose (4312.5 parts) are mixed with a mixer (Type DC, manufactured by Astellas Pharma Inc.). 200 mg of this mixture is filled into a capsule (gelatin hard capsule No. 4, manufactured by Capsugel Japan Inc.) with a small-scale capsule filling machine (propyl, manufactured by Capsugel Japan Inc.) to obtain a capsule.

Example 5

Preparation of the Capsule According to the Present Invention (3)

(3R)-Quinuclidin-3-yl (1S)-1-phenyl-1,2,3,4-tetrahydroisoquinoline-2-carboxylate succinate (185 parts), (R)-2-(2-aminothiazol-4-yl)-4'-{2-[(2-hydroxy-2-phenylethyl)amino]ethyl}acetanilide (1850 parts), and lactose (2960 parts) are mixed with a mixer (Type DC, manufactured by Astellas Pharma Inc.). 270 mg of this mixture is filled into a capsule (gelatin hard capsule No. 3, manufactured by Capsugel Japan Inc.) with a small-scale capsule filling machine (propyl, manufactured by Capsugel Japan Inc.) to obtain a capsule.

From the results above, it is obvious that a combination use of (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof as active ingredients of the pharmaceutical composition according to the present invention or combined agent supposed to be used simultaneously in combination enables inhibition of the increase in the intravesical pressure, and is useful as a therapeutic agent for overactive bladder. Moreover, it was confirmed that its effect is unexpectedly superior to that of the combination of propiverine hydrochloride and (−)-ethyl-2-[4-(2-{[(1S,2R)-2-hydroxy-2-(4-hydroxyphenyl)-1-methylethyl]amino}ethyl)-2,5-dimethylphenyloxy]acetate monohydrochloride, specifically known as Example 4 of Patent Document 1.

INDUSTRIAL APPLICABILITY

The pharmaceutical composition containing (R)-2-(2-aminothiazol-4-yl)-4'-{2-[(2-hydroxy-2-phenylethyl)amino]ethyl}acetanilide or a pharmaceutically acceptable salt thereof and (3R)-quinuclidin-3-yl (1S)-1-phenyl-1,2,3,4-tetrahydroisoquinoline-2-carboxylate or a pharmaceutically acceptable salt thereof as active ingredients can be used as a therapeutic agent for urinary urgency, pollakiuria and/or urinary incontinence accompanying overactive bladder.

The invention claimed is:

1. A pharmaceutical composition, comprising: (i) (R)-2-(2-aminothiazol-4-yl)-4'-{2-[(2-hydroxy-2-phenylethyl)amino]ethyl}acetanilide or a pharmaceutically acceptable salt thereof present from 25 to 50 mg in terms of (R)-2-(2-aminothiazol-4-yl)-4'-{2-[(2-hydroxy-2-phenylethyl)amino]ethyl}acetanilide and (ii) (3R)-quinuclidin-3-yl (1S)-1-phenyl-1,2,3,4-tetrahydroisoquinoline-2-carboxylate or a pharmaceutically acceptable salt thereof present at 5 mg in terms of (3R)-quinuclidin-3-yl (1S)-1-phenyl-1,2,3,4-tetrahydroisoquinoline-2-carboxylate succinate.

2. The pharmaceutical composition of claim 1, wherein the (R)-2-(2-aminothiazol-4-yl)-4'-{2-[(2-hydroxy-2-phenylethyl)amino]ethyl}acetanilide or a pharmaceutically acceptable salt thereof is (R)-2-(2-aminothiazol-4-yl)-4'-{2-[(2-hydroxy-2-phenylethyl)amino]ethyl}acetanilide.

3. The pharmaceutical composition of claim 2, wherein the (3R)-quinuclidin-3-yl (1S)-1-phenyl-1,2,3,4-tetrahydroisoquinoline-2-carboxylate or a pharmaceutically acceptable salt thereof is (3R)-quinuclidin-3-yl (1S)-1-phenyl-1,2,3,4-tetrahydroisoquinoline-2-carboxylate succinate.

4. The pharmaceutical composition of claim 1, wherein the (3R)-quinuclidin-3-yl (1S)-1-phenyl-1,2,3,4-tetrahydroisoquinoline-2-carboxylate or a pharmaceutically acceptable salt thereof is (3R)-quinuclidin-3-yl (1S)-1-phenyl-1,2,3,4-tetrahydroisoquinoline-2-carboxylate succinate.

5. A method for treating urinary urgency, pollakiuria and/or urinary incontinence accompanying overactive bladder, comprising administering effective amounts of (i) (R)-2-(2-aminothiazol-4-yl)-4'-{2-[(2-hydroxy-2-phenylethyl)amino]ethyl}acetanilide or a pharmaceutically acceptable salt thereof at a dosage of 25 to 50 mg in terms of (R)-2-(2-aminothiazol-4-yl)-4'-{2-[(2-hydroxy-2-phenylethyl)amino]ethyl}acetanilide, and (ii) (3R)-quinuclidin-3-yl (1S)-1-phenyl-1,2,3,4-tetrahydroisoquinoline-2-carboxylate or a pharmaceutically acceptable salt thereof at a dosage of 5 mg in terms of (3R)-quinuclidin-3-yl (1S)-1-phenyl-1,2,3,4-tetrahydroisoquinoline-2-carboxylate succinate.

6. The method claim 5, wherein said (R)-2-(2-aminothiazol-4-yl)-4'-{2-[(2-hydroxy-2-phenylethyl)amino]ethyl}acetanilide or pharmaceutically acceptable salt thereof, and said (3R)-quinuclidin-3-yl (1S)-1-phenyl-I,2,3,4-tetrahydroisoquinoline-2-carboxylate or pharmaceutically acceptable salt thereof are both administered orally.

7. The method for treating of claim 5, wherein said (R)-2-(2-aminothiazol-4-yl)-4'-{2-[(2-hydroxy-2-phenylethyl)amino]ethyl}acetanilide or pharmaceutically acceptable salt thereof and said (3R)-quinuclidin-3-yl (1S)-I-phenyl-I,2,3,4-tetrahydroisoquinoline-2-carboxylate or pharmaceutically acceptable salt thereof are administered simultaneously.

8. The method of claim 7, wherein said (R)-2-(2-aminothiazol-4-yl)-4'-{2-[(2-hydroxy-2-phenylethyl)amino]ethyl}acetanilide or pharmaceutically acceptable salt thereof, and said (3R)-quinuclidin-3-yl (1S)-I-phenyl-I,2,3,4-tetrahydroisoquinoline-2-carboxylate or pharmaceutically acceptable salt thereof are both administered orally.

9. The method of claim 5, wherein said (R)-2-(2-aminothiazol-4-yl)-4'-{2-[(2-hydroxy-2-phenylethyl)amino]ethyl}acetanilide or pharmaceutically acceptable salt thereof and said (3R)-quinuclidin-3-yl (1S)-I-phenyl-I,2,3,4-tetrahydroisoquinoline-2-carboxylate or pharmaceutically acceptable salt thereof are administered at a time interval.

10. The method of claim 9, wherein said (R)-2-(2-aminothiazol-4-yl)-4'-{2-[(2-hydroxy-2-phenylethyl)amino]ethyl}acetanilide or pharmaceutically acceptable salt thereof, and said (3R)-quinuclidin-3-yl (1S)-I-phenyl-I,2,3,4-tetrahydroisoquinoline-2-carboxylate or pharmaceutically acceptable salt thereof are both administered orally.

11. The method of claim 5, wherein said (R)-2-(2-aminothiazol-4-yl)-4'-{2-[(2-hydroxy-2-phenylethyl)amino]ethyl}acetanilide or pharmaceutically acceptable salt thereof is (R)-2-(2-aminothiazol-4-yl)-4'-{2-[(2-hydroxy-2-phenylethyl)amino]ethyl}acetanilide, and said (3R)-quinuclidin-3-yl (1S)-1-phenyl-1,2,3,4-tetrahydroisoquinoline-2-carboxylate or pharmaceutically acceptable salt thereof is (3R)-quinuclidin-3-yl (1S)-1-phenyl-1,2,3,4-tetrahydroisoquinoline-2-carboxylate succinate.

12. The method of claim 11, wherein said (R)-2-(2-aminothiazol-4-yl)-4'-{2-[(2-hydroxy-2-phenylethyl)amino]ethyl}acetanilide, and said (3R)-quinuclidin-3-yl (1S)-1-phenyl-1,2,3,4-tetrahydroisoquinoline-2-carboxylate succinate are both administered orally.

13. The method of claim 11, wherein said (R)-2-(2-aminothiazol-4-yl)-4'-{2-[(2-hydroxy-2-phenylethyl)amino]ethyl}acetanilide and said (3R)-quinuclidin-3-yl (1S)-1-phenyl-1,2,3,4-tetrahydroisoquinoline-2-carboxylate succinate are administered simultaneously.

14. The method of claim 13, wherein said (R)-2-(2-aminothiazol-4-yl)-4'-{2-[(2-hydroxy-2-phenylethyl)amino]ethyl}acetanilide, and said (3R)-quinuclidin-3-yl (1S)-1-phenyl-1,2,3,4-tetrahydroisoquinoline-2-carboxylate succinate are both administered orally.

15. The method of claim 11, wherein said (R)-2-(2-aminothiazol-4-yl)-4'-{2-[(2-hydroxy-2-phenylethyl)amino]ethyl}acetanilide and said (3R)-quinuclidin-3-yl (1S)-1-phenyl-1,2,3,4-tetrahydroisoquinoline-2-carboxylate succinate are administered at a time interval.

16. The method of claim 15, wherein said (R)-2-(2-aminothiazol-4-yl)-4'-{2-[(2-hydroxy-2-phenylethyl)amino]ethyl}acetanilide, and said (3R)-quinuclidin-3-yl (1S)-1-phenyl-1,2,3,4-tetrahydroisoquinoline-2-carboxylate succinate are both administered orally.

* * * * *

UNITED STATES PATENT AND TRADEMARK OFFICE
CERTIFICATE OF CORRECTION

| | | |
|---|---|---|
| PATENT NO. | : 8,772,315 B2 | Page 1 of 2 |
| APPLICATION NO. | : 13/748956 | |
| DATED | : July 8, 2014 | |
| INVENTOR(S) | : Masanori Suzuki et al. | |

It is certified that error appears in the above-identified patent and that said Letters Patent is hereby corrected as shown below:

ON THE TITLE PAGE AT ITEM (56) FOREIGN PATENT DOCUMENTS

"WO   96/20194   7/1996" should read --WO   1996/20194   7/1996--.

IN THE SPECIFICATION

COLUMN 1:

Line 57, "nate takes place" should read --nation arises--.

COLUMN 11:

Line 21, "A value" should read --¶A value--.

IN THE CLAIMS

COLUMN 13:

Line 38, "(1S)-I-phenyl-I,2,3,4-tetrahy-" should read --(1S)-1-phenyl-1,2,3,4-tetrahy- --.

COLUMN 14:

Line 1, "claim 5," should read --of claim 5,--;
Line 4, "(1S)-1-phenyl-I,2,3,4-tet-" should read --(1S)-1-phenyl-1,2,3,4-tet- --;
Line 7, "for treating" should be deleted;
Line 10, "(1S)-I-phenyl-I,2,3,4-" should read --(1S)-1-phenyl-1,2,3,4- --;
Line 16, "(1S)-I-phenyl-I,2,3,4-tetrahy-" should read --(1S)-1-phenyl-1,2,3,4-tetrahy- --;

Signed and Sealed this
Fourteenth Day of October, 2014

Michelle K. Lee
*Deputy Director of the United States Patent and Trademark Office*

Line 22, "(1S)-I-phenyl-I,2,3,4-tetrahy-" should read --(1S)-1-phenyl-1,2,3,4-tetrahy- --;
and Line 28, "(1S)-I-phenyl-I,2,3,4-tetrahy-" should read --(1S)-1-phenyl-1,2,3,4-tetrahy- --.